United States Patent
Ebi et al.

(10) Patent No.: US 7,654,824 B2
(45) Date of Patent: Feb. 2, 2010

(54) EXTENSION PIECE FOR A DENTAL IMPLANT, TRANSFER AID FOR TRANSFERRING THE POSITION OF AN IMPLANT AND OF AN EXTENSION PIECE, AND METHOD FOR PRODUCING A BASIS FOR A RETENTION ELEMENT

(75) Inventors: Daniel Ebi, Liestal (CH); Holger Herweg, Freiburg (DE)

(73) Assignee: Straumann Holding AG, Basel (CH)

( * ) Notice: Subject to any disclaimer, the term of this patent is extended or adjusted under 35 U.S.C. 154(b) by 287 days.

(21) Appl. No.: 10/771,572

(22) Filed: Feb. 4, 2004

(65) Prior Publication Data
US 2004/0180308 A1 Sep. 16, 2004

(30) Foreign Application Priority Data
Feb. 5, 2003 (EP) .................................. 03100245

(51) Int. Cl.
*A61C 8/00* (2006.01)
(52) U.S. Cl. ........................................ 433/214; 433/173
(58) Field of Classification Search ................. 433/172, 433/173, 174, 213, 214
See application file for complete search history.

(56) References Cited

U.S. PATENT DOCUMENTS

| | | | |
|---|---|---|---|
| 5,564,924 A | 10/1996 | Kwan | |
| 5,688,123 A * | 11/1997 | Meiers et al. | 433/173 |
| 5,733,124 A | 3/1998 | Kwan | |
| 5,904,483 A * | 5/1999 | Wade | 433/173 |
| 5,947,736 A | 9/1999 | Behrend | 433/214 |
| 6,068,478 A * | 5/2000 | Grande et al. | 433/172 |
| 6,213,773 B1 * | 4/2001 | Gittleman | 433/172 |
| 6,283,752 B1 * | 9/2001 | Kumar | 433/172 |

(Continued)

FOREIGN PATENT DOCUMENTS

JP 11-500039 1/1999

(Continued)

OTHER PUBLICATIONS

European Search Report (in German) dated Jul. 9, 2003.

*Primary Examiner*—Ralph A Lewis
(74) *Attorney, Agent, or Firm*—Rissman, Hendericks & Oliverio, LLP

(57) ABSTRACT

An extension piece (2) for a dental implant (1) has a head part (20) which serves as a basis for a retention element (7). The extension piece (2) can be screwed in the dental implant (1) with a threaded stem (29). The extension piece (2) is provided with a reference surface (24) via which the position of the extension piece (2) in the circumferential direction can be transferred to a transfer aid (4) having a transfer surface (42) shaped to complement the reference surface (24). The position of the extension piece (2) is transferred via the transfer aid (4) into an impression (93). The extension piece (2) is then provided with a manipulation implant (5) and is repositioned in the impression (93). From this, a working model (M) is formed in which the desired shape of the extension piece (2) can be defined. The extension piece (2) which has been machined to the desired shape is then screwed into the implant (1) with the same torque as is used for taking the impression.

26 Claims, 14 Drawing Sheets

U.S. PATENT DOCUMENTS

| | | | |
|---|---|---|---|
| 6,332,777 B1 * | 12/2001 | Sutter | 433/173 |
| 6,508,650 B2 * | 1/2003 | Gittleman | 433/172 |
| 6,540,514 B1 * | 4/2003 | Falk et al. | 433/173 |
| 6,726,480 B1 | 4/2004 | Sutter | |
| 6,758,672 B2 * | 7/2004 | Porter et al. | 433/173 |
| 6,824,386 B2 * | 11/2004 | Halldin et al. | 433/173 |
| 7,066,736 B2 * | 6/2006 | Kumar et al. | 433/173 |
| 2001/0000748 A1 | 5/2001 | Rogers et al. | |
| 2001/0034008 A1 | 10/2001 | Porter | 433/172 |
| 2002/0127515 A1 | 9/2002 | Gittleman | 433/172 |
| 2002/0142266 A1 | 10/2002 | Rogers et al. | |
| 2004/0209226 A1 | 10/2004 | Rogers et al. | |

FOREIGN PATENT DOCUMENTS

| | | |
|---|---|---|
| JP | 2000-512882 | 10/2000 |
| JP | 2001-518348 | 10/2001 |

* cited by examiner

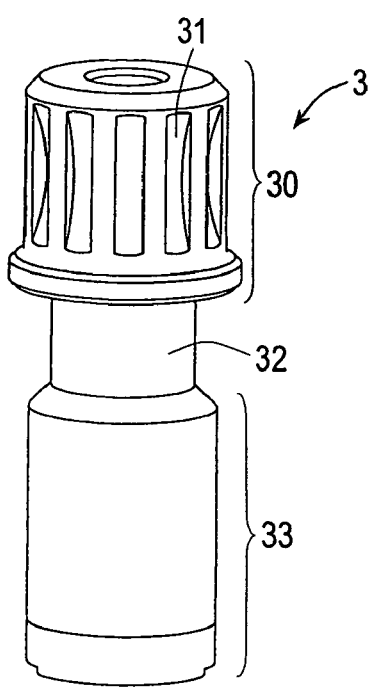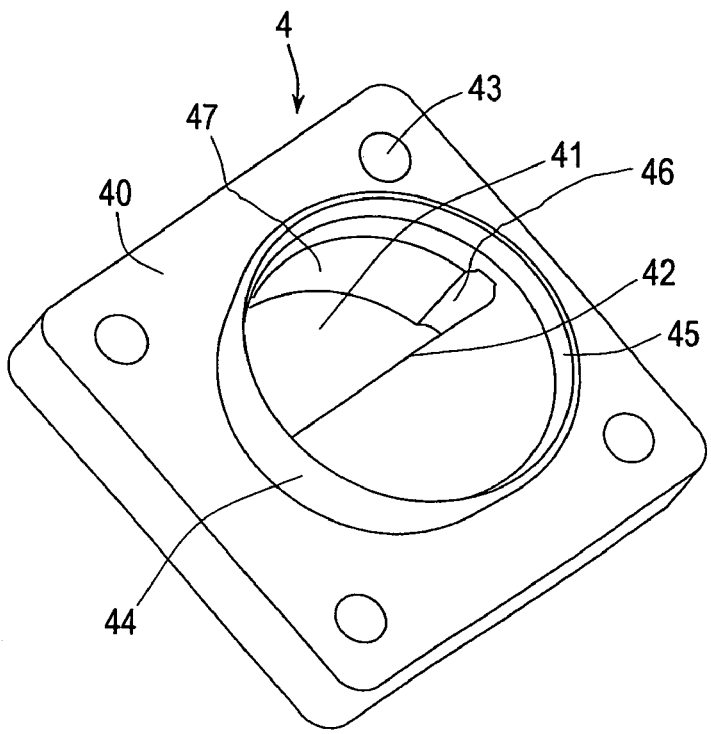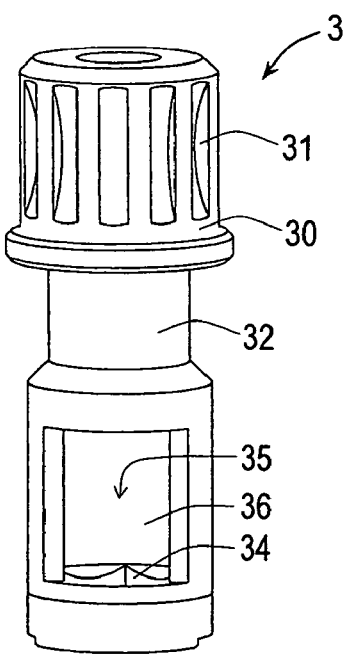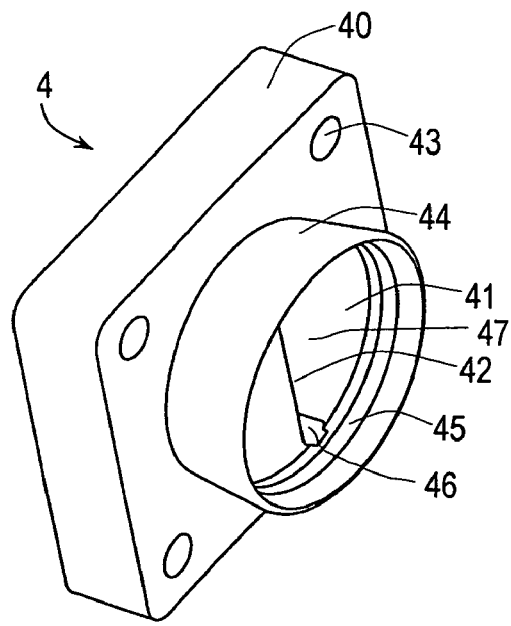
Fig. 3A
Fig. 4A
Fig. 3B
Fig. 4B

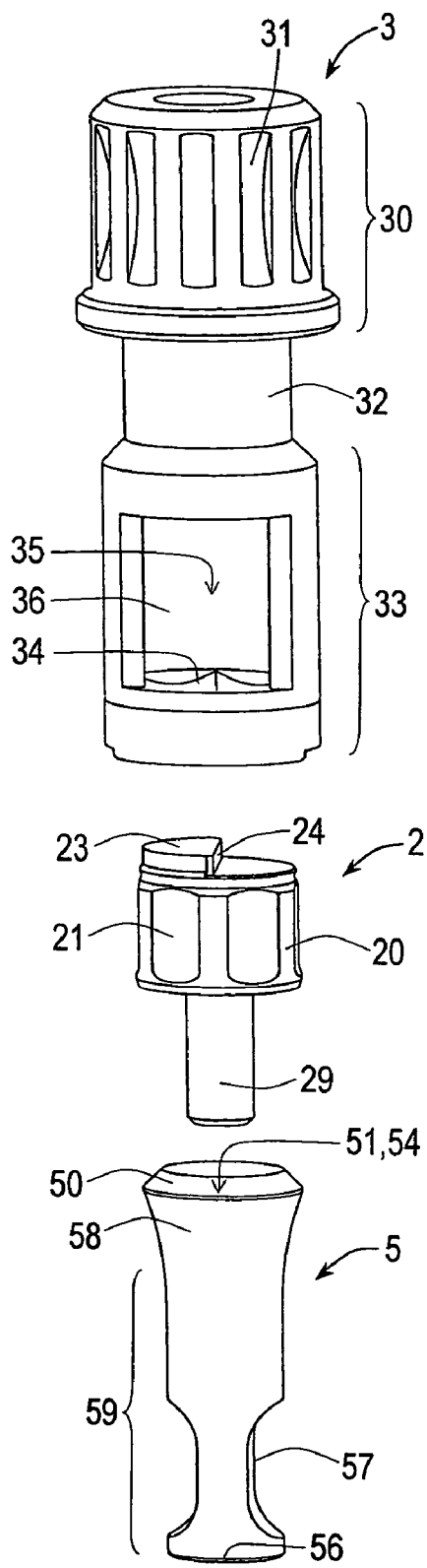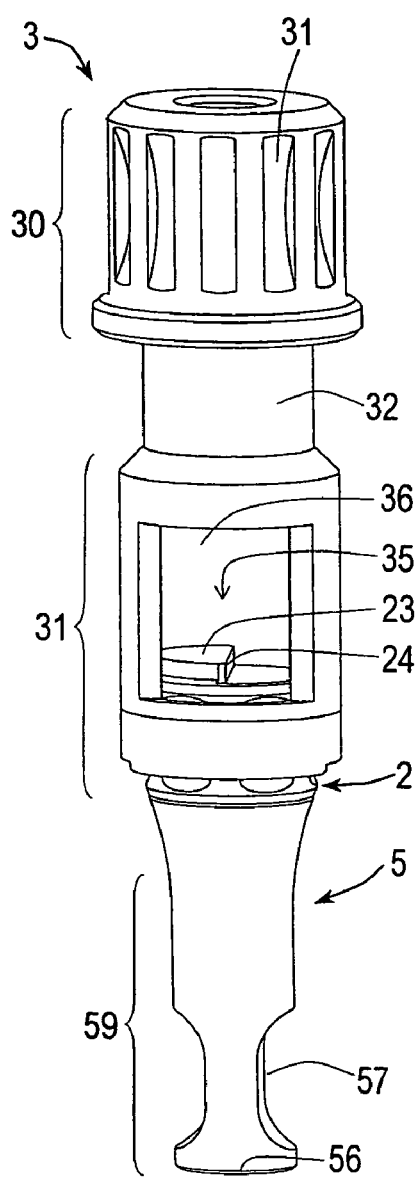
Fig. 13A
Fig. 13B

EXTENSION PIECE FOR A DENTAL IMPLANT, TRANSFER AID FOR TRANSFERRING THE POSITION OF AN IMPLANT AND OF AN EXTENSION PIECE, AND METHOD FOR PRODUCING A BASIS FOR A RETENTION ELEMENT

RELATED APPLICATIONS

This application claims benefit of priority under 35 U.S.C. § 119 to European Patent Application 03 100 245.5, filed Feb. 5, 2003.

FIELD OF THE INVENTION

The invention relates to one or more of an extension piece for a dental implant, a transfer aid for transferring the position of a dental implant and of an extension piece to a working model, and a method for producing a basis for a retention element and for taking an impression of the radial and axial position of a dental implant with an extension piece.

BACKGROUND OF THE INVENTION

It is known to apply extension pieces to dental implants which are implanted in a patient's jaw bone, said extension pieces serving as a support structure for tooth attachments. Such extension pieces are often also called abutments or secondary parts.

The extension pieces are also used for fixing tooth prostheses with several teeth. A tooth prosthesis is typically secured on several such extension pieces held on implants. In this connection, it is important that the axial direction of the extension pieces is parallel, even when the fitted implants are not precisely parallel, so that the prosthesis can be applied in a defined direction of application. It is already known to machine extension pieces so that a defined direction of application can be achieved (see, for example, Technoinfo "Die Anwendung des Fräszylinders für das Octa-System" [Use of the milling cylinder for the Octa system] by Straumann).

It is also known to provide the extension piece with what is called a ball anchor. The extension piece which can be screwed into the implant is in this case provided on its top face with a ball-like projection on which a prosthesis can be held by means of corresponding holding elements in the manner of a press-button (see, for example, Technoinfo, "Die Anwendung des retentiven Kugelankers" [Use of the retentive ball anchor] by Straumann or "Das Bone Graft System" [The bone Graft System] by Straumann).

It is also generally known to transfer the situation of implants and extension pieces in a patient's mouth to a working model. The dental technician then produces the tooth prosthesis using the position of the implants and of the extension pieces in the working model. To transfer the situation to the working model, impression-taking elements are used which transfer the axial and radial position of implant and extension piece into an impression compound. Impression caps are known which are screwed to the implant. However, impression caps are also known which can be snapped or clamped onto an implant shoulder (see, for example, EP 879 024) or onto an extension piece (see, for example, DE 44 15670). From WO 02/087461, an implant is also known in which the implant is secured in a storage container by means of an impression cap.

The impression cap is used while an impression is being taken of the situation in the patient's mouth, and it remains in the impression compound when the impression compound is removed from the implant.

However, all of these known extension pieces and transfer aids are associated with certain disadvantages if the extension piece serves as a basis for a retention element for a tooth prosthesis. Particularly in the case of implants which are not fitted exactly parallel to one another, it is difficult to machine and fit a plurality of extension pieces in such a way that the direction of application of a prosthesis is parallel for all the fitted extension pieces. The use of known impression-taking systems is unsatisfactory for this purpose. Known impression-taking systems do not permit an impression of the course of the internal thread on the implant, because the thread start is not in a predefined relationship to reference surfaces, for example an internal octagon, provided on an implant. It is therefore not possible to take an impression of the thread course by referencing of such surfaces.

A determination of the position of the implant in the circumferential direction is not possible when using solid secondary parts, because this secondary part/extension piece covers the reference surfaces provided on the internal contour of the implant for definition of the circumferential direction.

The secondary part disclosed in EP 879 924 serves in particular for supporting a single tooth replacement. The secondary part is not suitable as a basis for a retention element. Taking an impression on a non-rotationally symmetrical reference surface of the extension piece, as shown in EP 879 024, is likewise associated with disadvantages in terms of the use of the extension piece as a basis for a retention element. On the one hand, the exact position of the extension piece in the axial direction and in the circumferential direction is not precisely defined because of the mutual bearing of the extension piece and the internal contour of the implant in a relatively steep cone surface.

On the other hand, the relationship between the thread start of the extension piece and the reference surface on the extension piece is not always exactly defined in the case of extension pieces which serve as a basis for a retention element, and which are typically made of precious metal. The use of a manipulation implant with an element identical to the extension piece and formed integrally with the manipulation implant (as shown in EP 879 024) is therefore also difficult.

SUMMARY OF THE INVENTION

In accordance with one or more implementations of the invention, an apparatus and/or method are provided to create an extension piece for a dental implant, which extension piece permits a parallel direction of application of a tooth replacement to be secured on the extension piece, even when the implants fitted are not parallel to one another. Also provided are a transfer aid and a method by which the position of the implant and of the extension piece in a patient's mouth can be transferred reliably, in a simple manner, to a working model. In select implementations, the impression-taking method and the impression-taking system and the extension piece should be simple to use and as inexpensive as possible to produce.

According to one or more implementations of the invention, there is provided an extension piece, a transfer aid and a method having the features set out in the claims.

The extension piece for a dental implant according to the one implementation has a head part. The head part serves as a basis for a retention element. The retention element is used for securing a tooth replacement. The extension piece is additionally provided with a threaded stem, by means of which it can be screwed into the dental implant. According to one implementation, the extension piece has at least one reference form, by means of which the position of the extension piece, seen in the circumferential direction, can be transferred to a working model. The reference form used can be any desired configuration on the extension piece permitting transfer of the position of the extension piece, as seen in the circumferential direction. The reference form can typically be a non-rotationally symmetrical reference surface. However, it can also be formed, for example, by a suitably arranged bore on the extension piece. Here, and in the following, the term reference surface is used generically to denote any conceivable type of geometric form permitting transfer of the position of the extension piece in the circumferential direction. By virtue of the at least one reference surface, the position of the extension piece in the circumferential direction can be precisely determined and transferred to the working model. For each individual extension piece, there is an exactly defined relationship between the position of the reference surface and the thread start on the threaded stem. This relationship can be transferred to the working model if the extension piece is used as transfer aid, in the manner described below. Typically, the reference surface is not rotationally symmetrical.

According to one or more implementations of the invention, the extension piece has a mating shoulder via which the extension piece can be supported on a shoulder of the implant. Because of the contact between mating shoulder and implant shoulder, the position of the extension piece can be precisely defined in the axial direction, since it is not defined, as in EP 879 024 for example, by contact between two steep cone surfaces. The circumferential position is referenced by the reference surface, the axial position by the contact of the shoulder.

According to one or more implementations, the extension piece transfer contour has a first contour onto which a complementarily shaped second contour can be clamped and/or snapped. With this transfer aid, the position of the extension piece in the impression compound can be more precisely defined and retained, as is described below, while the impression is being taken.

According to a particularly preferred illustrative embodiment, the head part is of substantially cylindrical design. The reference surface in this case is advantageously formed by a cut edge extending parallel to the screw axis of the extension piece, so that the extension piece at its upper end is formed by a half cylinder. Such a reference surface is particularly simple to produce. This reference surface, which is no longer needed upon definitive application of the extension piece to the implant, can also be easily removed, during machining of the extension piece, to receive a retention element. In addition, a reference surface designed in this way is especially suitable for use in conjunction with a simply designed transfer aid.

According to a further preferred embodiment, the extension piece additionally has a non-cylindrical outer contour with gripping surfaces. The extension piece can easily be screwed into an implant with the aid of a tool which engages on the gripping surfaces. In this way, it is possible to precisely control the screwing-in force in the manner described below.

It is also conceivable and preferable to provide a bevel in the area of the transition from the reference surface to the outer surface of the semicircular cylinder. On the one hand the bevel prevents damage to the plastic transfer aid described below. Application of a transfer aid of this kind is also made easier by virtue of the bevel.

As has been described above, the extension piece serves as a basis for a retention element. Such retention elements can be secured, for example, by soldering. According to a preferred embodiment, the extension piece material is composed of a metallic, non-oxidizing, high-melting-point alloy. For example, the composition can contain 60% Au, 19% Pt, 20% Pd, and 1% Ir. The melting range of this alloy is typically between 1400° and 1490°.

The transfer aid according to one or more implementations is used to transfer the position of an implant, and of an extension piece secured therein, in axial direction and in circumferential direction, to a working model. The transfer aid has a transfer form designed to complement a reference form on an extension piece. The transfer form used can be any desired configuration which permits a definition of the position of the transfer aid in the circumferential direction. The transfer form can typically be designed as a reference surface cut out from a cylinder surface. However, other forms are also conceivable, for example projections or depressions on the transfer aid. Here, and in the description below, the term transfer surface is used as a generic designation for any configuration which permits referencing in the circumferential direction. The transfer surface can therefore also be part of a partially rotationally symmetrical form, for example formed by a polygon. For reasons of clarity, however, preference is given to non-rotationally symmetrical surfaces which can be made congruent only in one position.

The transfer aid according to one or more implementations has a base plate in which the transfer surface is arranged. The transfer aid is also provided with clamping and/or snap-fit means, by means of which it can be secured on the extension piece. The base plate has a form which can be anchored in an impression compound. The form should be chosen such that rotation of the transfer aid in the impression compound is prevented. The base plate can typically have a non-rotationally symmetrical outer contour and/or can be provided with holes through which the impression compound can pass and which likewise prevent rotation of the transfer aid. To prevent aspiration during application of the impression aid onto the extension piece, the impression aid can secured with a thread.

According to a preferred illustrative embodiment, the transfer surface of the transfer aid is part of a wall of a semicylindrical opening in the base plate. The semicylindrical opening has a cut edge which extends perpendicular to the axis of the transfer aid and which is designed to complement, and be brought into contact with, a cut edge of a half cylinder on the head part of an extension piece, as has been described above. A recess can also be provided in the transition area between the transfer surface and the semicylindrical inner surface of the opening. The transfer aid is typically produced by plastic injection-molding. This can generate corners that are not quite precisely defined. Roundings in the area of the transition could mean that the transfer aid could be fitted poorly onto the corresponding extension piece. This problem is eliminated by the additional recess.

The clamping and/or snap-fit means of the transfer aid according to one or more implementations can particularly preferably be formed by a circular lip which is arranged on the base plate and which has a second contour, in particular a bead, which is designed to complement a first contour, especially designed as a groove, of the extension piece and can be snapped and/or clamped onto it. Of course, it is also possible to provide a groove on the transfer aid, and a bead on the extension piece.

The transfer aid is preferably designed in one piece, typically made of an elastic plastic material. Such a transfer aid is, on the one hand, easy and inexpensive to produce, for example by injection molding. On the other hand, such a choice of material permits simple snap-fitting.

In a further preferred illustrative embodiment, the opening in the transfer aid can in particular extend transversely right through the base plate. On one side, the extension piece can be inserted with the reference surface into the opening. On the other side, impression compound can pass through the opening in the base plate and reach as far as the extension piece inserted into the transfer aid and can thus precisely define the position of the latter together with the transfer aid.

According to a further preferred illustrative embodiment, the base plate of the transfer aid has holes which, as has been described above, serve to safeguard against aspiration.

A further aspect of one or more implementations lies in the use of an extension piece which can be machined, in particular ground, for a dental implant, as a transfer part for transferring its position on a dental implant in the axial and circumferential directions, and as a basis for a retention element. The extension piece is therefore used not for only as a basis for a retention element, but also transferring its own position in a firmly screwed state on the implant. In this way, it is possible to dispense with an additional transfer part, such as is described for example in EP 879 024. Sources of error are minimized. In particular, the relationship between transfer surface and thread start, which relationship is individual to each extension piece, is precisely maintained.

A further aspect of one or more implementations lies in the combination of a transfer aid, as described above, with an extension piece, as described above. The transfer surface of the transfer aid is in this case designed complementing the reference surface of the extension piece.

The method according to one or more implementations serves in the first, instance for taking an impression of the position, in circumferential direction and axial direction, of a dental implant implanted in a patient's jaw bone, and of an extension piece secured thereon, and transferring this to a working model. The method according to the invention additionally concerns the production of a basis, for a retention element, which can be screwed into the implant. Taking the impression of the situation in the mouth is the first step of the method.

In the method according to one or more implementations, an extension piece as a basis for a retention element is firstly screwed into each implant provided for this purpose in the patient's mouth. Here, and in the text below, the method is illustrated with reference to an implant with an extension piece. Of course, the method is advantageously used in particular with several implants and/or abutments (for example a residual dentition with tooth stumps which, in addition to implants, support a basis for a retention element). The screwing is done with a predetermined first torque. In this way, it is possible to ensure that the position of the extension piece in the implant can be precisely reproduced.

In the next step, an impression of the situation of the implant and of the extension piece in the patient's mouth is produced. To do this, an impression compound is applied to the implant in a manner known per se. The impression compound is removed after hardening. After removal of the impression compound from the mouth, the anchoring piece remains connected to the implant. The shape of the extension piece, in particular the outer contour of the head part, is maintained in the impression compound.

The extension piece is then unscrewed from the implant and repositioned in the correct position in the impression compound. With a preferred, completely non-rotationally symmetrical arrangement of the reference surface, an unambiguous repositioning of the extension piece in the impression is possible.

With partial rotational symmetry, for example with a 180° symmetry, a number of positions are of course possible. Nevertheless, based on the knowledge of the setting, the user can reposition the extension piece precisely in the appropriate position.

Before or after the extension piece is repositioned in the impression, the extension piece is screwed with a second torque into a manipulation implant. This procedure can theoretically be done when the extension piece is already repositioned in the impression compound. However, the connection is preferably established before the extension piece is repositioned in the impression compound. This can be advantageous particularly for the reason that, with the manipulation implant, a fixture, as it were, is made available for the extension piece, so that handling of said extension piece is easier. Moreover, there is no risk of the extension piece being subsequently turned in the impression by unscrewing of the manipulation implant.

The impression-taking is done in common for all implants and all extension pieces. The removal of the extension pieces from the implants and the repositioning of the extension pieces in the impression are done individually.

In a last step, a working model is produced by casting the manipulation implant or implants secured on the extension pieces in the impression into a modeling compound, for example plaster.

After removal of the impression compound from the cast-in manipulation implants and extension pieces, a working model is available in which the position of the extension pieces in the circumferential direction and in the axial direction corresponds precisely to the position of the extension pieces in the patient's mouth. A dental technician can now machine the extension pieces accordingly. In particular, the machining is carried out in such a way that retention elements can be secured on the extension pieces such that the direction of application is identical for all extension pieces and for all implants.

According to a preferred illustrative embodiment of the method according to the invention, a transfer aid is applied to the extension element before the removal of the impression of the extension element. The transfer aid can typically be applied by clamping or snap-fitting. Upon production of the impression, that is to say upon removal of the hardened impression compound, the transfer aid remains in the impression compound. By means of the transfer aid used, the repositioning of the extension piece in the impression is more precise and simpler.

According to a further preferred illustrative embodiment, the first predetermined torque is greater than the second torque. Typically, the first torque is approximately 35 Ncm. The second torque approximately corresponds to a manual screwing of the extension piece onto the manipulation implant. To ensure that the extension piece before impression-taking, and the machined extension piece after impression-taking and machining, is fitted in exactly the same position in the implant, it is important that the torque used for screwing into the implant is chosen exactly the same both times. For this purpose, a torque instrument is preferably used by means of which the torque can be chosen the same both times. It has been shown in practice that a torque of 35 Ncm is particularly suitable for securing the extension piece in the implant. The torque with which the manipulation implant is screwed onto the extension piece is less important. The exact position of the extension piece in the circumferential direction is set by the impression. Therefore, it suffices if the manipulation implant is screwed in by hand, that is to say without using a special tool.

According to a further preferred illustrative embodiment of the method according to the invention, in the first step the extension piece is turned twice in succession into the implant. In newly produced extension pieces, the thread on the threaded stem may have burrs or other irregularities. These irregularities are eliminated in the first screwing-in. In the second screwing-in, with a precisely predetermined torque, the same conditions then prevail as in the subsequent screwing-in of the machined extension piece with the same torque.

After the working model is produced, the extension piece is then advantageously machined, in particular ground. A basis for the retention element is formed in this way. The extension piece is machined, for example, by first arranging a position marking on the extension piece secured on the working model. The extension piece, for machining, can then be removed from the working model. For the machining, the extension piece can in particular be fitted onto a holder, provided for this purpose, and machined on the latter. However, it would also be possible in theory to machine the extension piece directly on the working model.

Moreover, a retention element for holding a detachable tooth replacement is preferably applied to the machined extension piece. The retention element can be secured, for example, by soldering, lasering or casting. However, other securing methods would also be conceivable. In this respect, it is conceivable for the retention element to be applied to the extension piece directly after the machining of the extension piece. However, it is also possible for the extension piece only to be prepared, and for the retention element to be applied at a later time by another user.

To ensure that the machined extension piece is in exactly the same position in the implant as it is when taking the impression, the machined extension piece is screwed into the implant with the same, first, predetermined torque as before taking the impression. The precise definition of the screwed-in extension piece relative to the implant can additionally be heightened by provision of a shoulder, as described above, which shoulder comes to bear on the implant shoulder when the extension piece is applied.

According to a further preferred illustrative embodiment of the method according to the invention, upon definitive screwing of the extension piece into the implant, a spreading cone is inserted between an inner cone, known per se, of the implant and the extension piece. The spreading cone can in particular increase the transverse stability of the extension piece on the implant. The force-fit connection via the implant shoulder and the cone leads to an optimum distribution of forces.

BRIEF DESCRIPTION OF THE DRAWINGS

The invention is explained in more detail with reference to illustrative embodiments and to the drawings, in which:

FIG. 3a: shows a perspective view of a screwing-in tool for screwing the extension piece into an implant/manipulation implant, FIG. 3b: shows a further perspective view of the screwing-in tool according to FIG. 3a, FIG. 4a: shows a perspective view of a transfer aid according to one embodiment of the invention FIG. 4b: shows a further perspective view of the transfer aid according to FIG. 4a, FIG. 5: shows a perspective view of a manipulation implant, FIGS. 9a-20c: show the principle outline of the method involving impression-taking, machining of the extension piece, application of a retention basis, and securing of the extension piece on the implant, in which figures:

FIG. 9a: shows the screwing of the extension piece into an implant,

FIG. 9b: shows the extension piece screwed into the implant,

FIG. 11: shows the process of taking an impression of the implant and of the extension piece screwed into the latter, FIG. 12: shows the removal of the impression from the implant and from the extension piece, FIG. 13a: shows how the extension piece is turned into a manipulation implant, FIG. 13b: shows the extension piece turned into the manipulation implant, FIGS. 20a-c: show how the finished extension piece is screwed into the implant.

DETAILED DESCRIPTION

Figure 1:
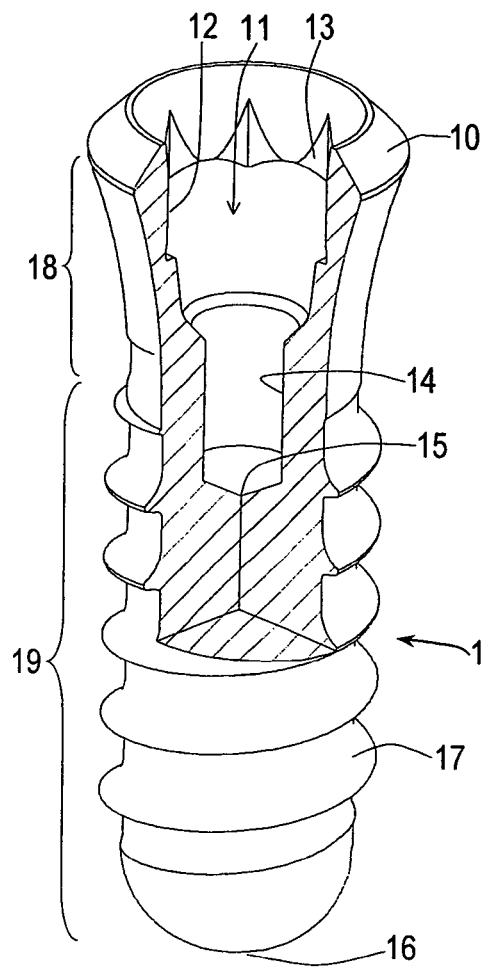
FIG. 1: shows a perspective view of an implant known per se, in partial section.

In the text below, identical reference numbers in each case designate identical parts. If reference numbers are shown in a drawing but are not explained in the directly associated text in the description, attention is drawn to their mention in the description of the preceding figures. Repeated indication of component parts in later figures is avoided where it is clear from the drawing that the parts concerned are components which have already been described.

FIG. 1 shows an implant 1 known per se which is designed as a solid screw implant. The implant 1 has a shank part 19 with an implant tip 16, and an implant head 18. The shank part 19 is intended to be screwed into a jaw bone. The implant head 18 protrudes at least partially from the jaw bone. The shank part 19 is provided with an external thread 17. The implant head ends in a known manner with an inclined implant shoulder 10. A blind bore 11 extending along the height of the implant head 18 opens out on said implant head 18. The blind bore 11 has an inner cone 12 and, arranged above the inner cone 12, an inner polygon 13. In standard use of the implant 1, the inner polygon 13 serves to define the position of the implant 1 in the circumferential direction. Arranged below the inner cone 12 there is an internal thread 14 into which an extension piece can be screwed. The opening in the implant is defined by a bore bottom 15.

Figure 2A:
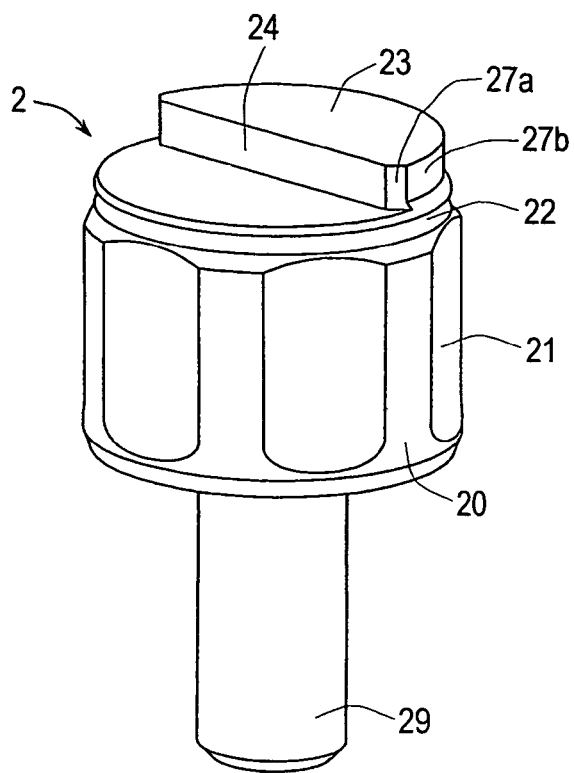
FIG. 2a: shows a perspective view of an extension piece according to one embodiment of the invention, seen from above.

FIG. 2a shows a perspective view of an extension piece 2 according to the invention. The extension piece 2 consists principally of a head part 20 and of a threaded stem 29 arranged at one end of the head part 20. For the sake of clarity, the thread of the threaded stem 29 is not shown. The head part 20 has several gripping surfaces 21 arranged in a polygonal formation. With the gripping surfaces 21, the extension piece 2 can be screwed tight using a suitable tool. Provided on the head part 20 there is a first contour 22 in the form of a peripheral groove. The first contour serves for engagement with a correspondingly shaped second contour 45 on a transfer aid (see FIGS. 4a and 4b).

The end of the head part 20 remote from the threaded stem 29 is designed as a semicircular cylinder section 23. The cylinder section 23 has a reference surface 24 which extends substantially diagonally. The reference surface 24 serves to define the position of the extension piece when an impression is being taken (see explanations of FIGS. 10a and 10b).

A bevel 27a is provided on the semicircular cylinder section 23 in the transition area between the reference surface 24 and the semicylindrical outer surface 27b of the cylinder section 23.

Figure 2B:
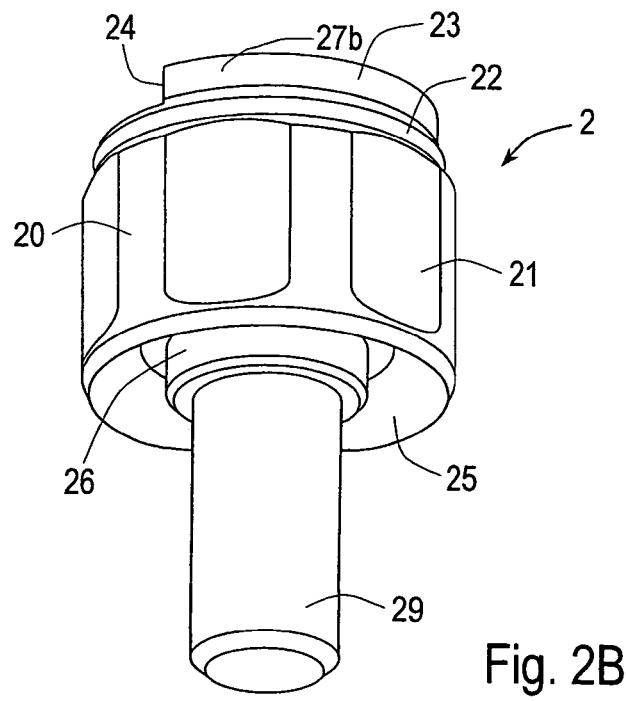
FIG. 2b: shows a perspective view of the extension piece according to one embodiment of the invention, as seen from below.

The extension piece 2 is shown from below in FIG. 2b. On the side intended for contact with the implant, the extension piece 2 has a mating shoulder 25 which is in contact with the implant shoulder 10 when the extension piece is applied. The inclination of the mating shoulder 25 is chosen to correspond to the inclination of the implant shoulder 10 and is typically 45°. The threaded stem 29 is additionally connected to a thickened area 26 which serves for contact with a spreading cone (see FIG. 8).

FIG. 3a shows a screwing-in tool 3 suitable for screwing the extension piece 2 in. The screwing-in tool 3 has a head 30 with a driver contour 31. The driver contour 31 is designed as a fluting. A torque instrument can engage in the driver contour 31. The screwing-in tool also has a neck part 32 and a shank part 33. Provided in the shank part 33 there is an inner contour 34 (see FIG. 3b) which corresponds to the gripping surfaces 21 of the extension piece 2. The inner contour 34 is part of a cavity 35 for receiving the head part 20. An opening 36 is provided in the shank part 33. The opening 36 permits attachment of the screwing-in tool to an extension piece with retention element secured thereon (see FIG. 20a for example), even when the retention element and/or the retention basis has in part a circumference greater than the free internal diameter of the screwing-in tool 3.

FIGS. 4a and 4b show perspective views of a transfer aid 4 according to one embodiment of the invention. The transfer aid 4 consists principally of a base plate 40 on which a circular lip 44 is arranged. An opening 41 is arranged in the base plate 40. The opening 41 serves to receive the semicircular cylinder section 23 of an extension piece 2. The opening 41 is delimited by a substantially diagonally extending transfer surface 42 and by a semicylindrical inner wall 47. Moreover, a recess 46 is additionally provided in the transition area between the semicylindrical inner surface 47 and the transfer surface 42. In the area of the transition, the recess 46 creates sufficient space to ensure that the transfer aid can be easily applied to a matching extension piece.

Holes 43 are also arranged in the base plate 40. The holes 43 serve for securing a thread as a safeguard against aspiration. A second contour in the form of a radial bead is additionally formed on the inside of the circular lip 44. The radial bead serves for engagement with the first contour 22 on the extension piece 2.

The transfer aid is made of a plastic material, for example PEEK, POM. The extension piece 2 is made of a metallic, non-oxidizing, high-melting-point alloy, typically with 60% Au, 19% Pt, 20% Pd, 1% Ir. The melting range of this alloy lies between 1400° and 1490° Celsius.

Figure 5:
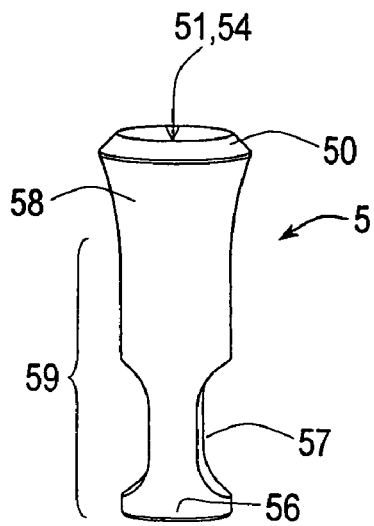

FIG. 5 shows a manipulation implant 5 by means of which the extension piece 2 can be positioned in a working model. The manipulation implant 5 is designed like the implant 2 and has a shank part 59 with a foot 56, and a head 58 with a shoulder 50. A blind bore 51 and an internal thread 54 are arranged in the head 58. The shank part 59 is provided with an outer contour 57 which is not 100% rotationally symmetrical and which is intended to prevent twisting of the manipulation implant.

Figure 6:
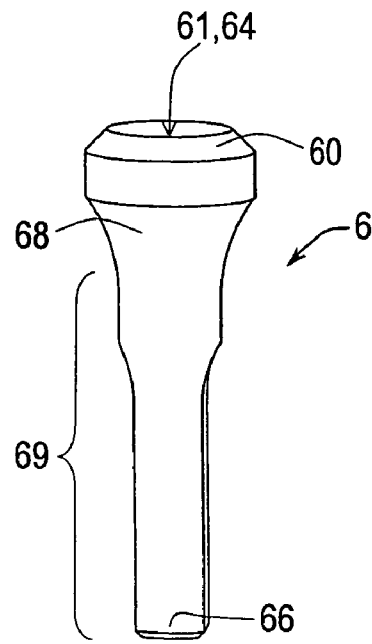
FIG. 6: shows a perspective view of a holder for holding the extension piece.

FIG. 6 shows a holder 6 for holding and machining the extension piece 2. The holder is likewise designed in principle like an implant 2 and, in particular, has a shoulder 60 and a blind bore 61 with an internal thread 64. The holder 6 has a shank part 69 via which the holder can be held and/or secured. The shank part 69 ends in a foot 66. The shank part 69 widens out, in the area of a head 68, toward the shoulder 60.

Figure 7:
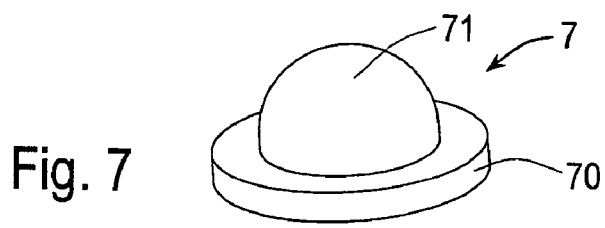
FIG. 7: shows a perspective view of a retention element.

FIG. 7 shows an example of a retention element 7. The retention element 7 consists of a disk 70 on which a head 71 is arranged. The head 71 serves to receive a tooth replacement.

Figure 8:
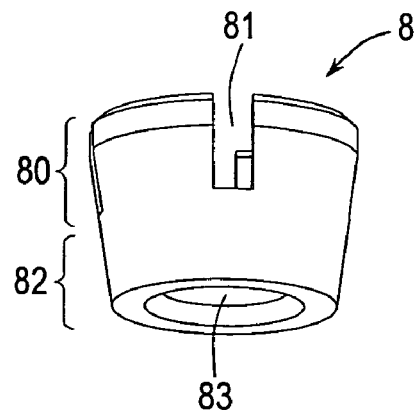
FIG. 8: shows a perspective view of a spreading cone.

FIG. 8 shows a spreading cone 8. The spreading cone has a head part 80. An expansion slit 81 is arranged in the head part 80. Extending below the head part 80 there is a conical wall part 82 on whose inside a thread is arranged. The spreading cone 8 has a passage 83 which extends in the axial direction and through which the threaded stem 29 of the extension piece 2 can be passed.

Figures 9A, 9B:
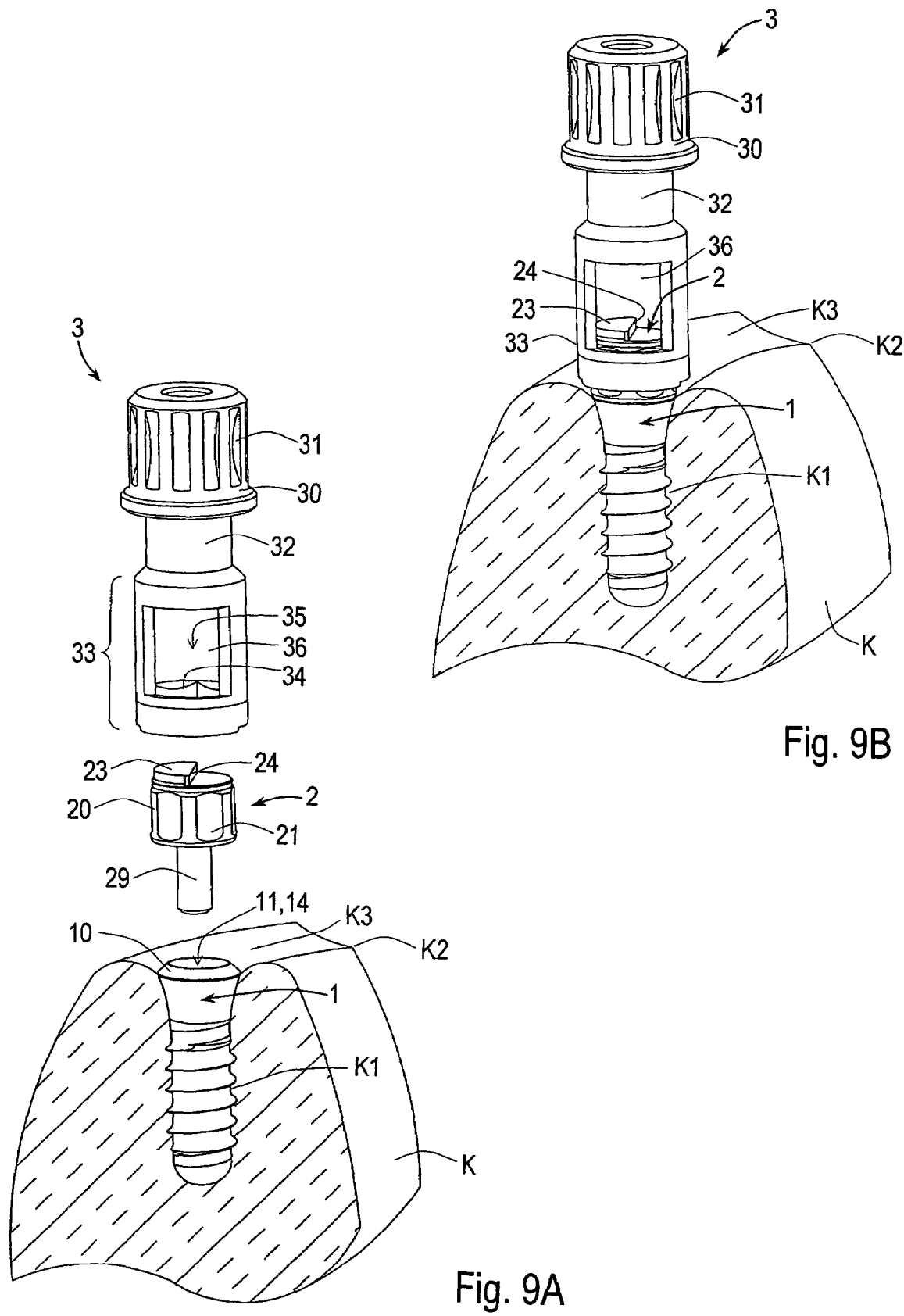

FIG. 9a shows an implant 1 which is fitted and has become incorporated in a hole K1 in the jaw bone K of a patient. The bone K has a bone crest K2 which defines a peripheral contour K3 in the area of the implant 1. In FIG. 9a, the screwing-in tool 3, the implant 1 and the extension piece 2 are shown separately. In the view in FIG. 9b, the extension piece 2, in a first step, is screwed into the implant 1 using the screwing-in tool 3. To do this, a torque attachment can be applied to the screwing-in tool 3 in a manner known per se, so that the extension piece 2 can be screwed in with an exactly defined torque (typically 35 Ncm). After the first screwing-in, the extension piece 2 is released and is screwed in a second time with the same torque. This avoids an inexactly defined end position of the extension piece 2 in the implant, caused by burrs or irregularities on the thread. When the extension piece 2 has been applied firmly to the implant 1, the screwing-in tool 3 is removed (see FIG. 9b).

Figure 10A:
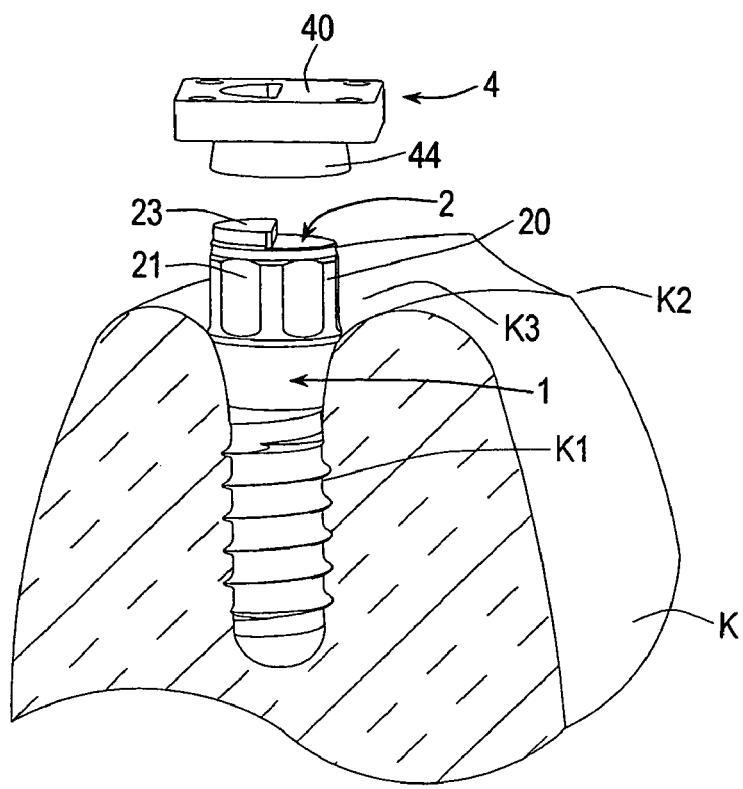
FIG. 10a: shows application of a transfer aid to an extension piece.

According to FIG. 10a, the transfer aid 4 is attached to the extension piece 2 in such a way that the semicircular cylinder section 23 on the extension piece 2 engages in the semicircular cylinder opening 41.

The transfer aid 4 snaps with the second contour 45 into the first contour 22 of the extension piece 2 and is held securely thereon.

Figure 10B:
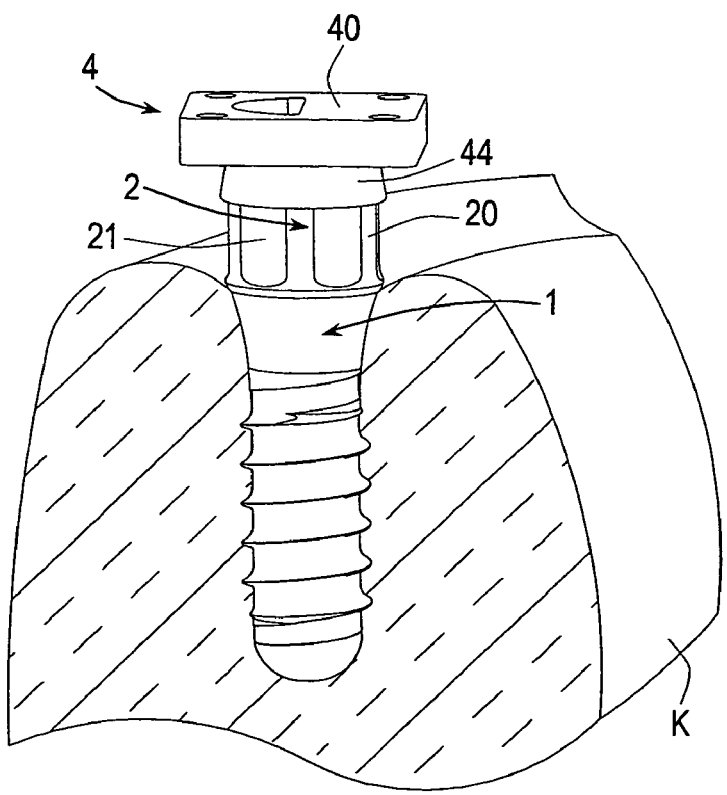
FIG. 10b: shows the transfer aid applied to the extension piece.

FIG. 10b shows the transfer aid 4 in the applied position.

Figure 10C:
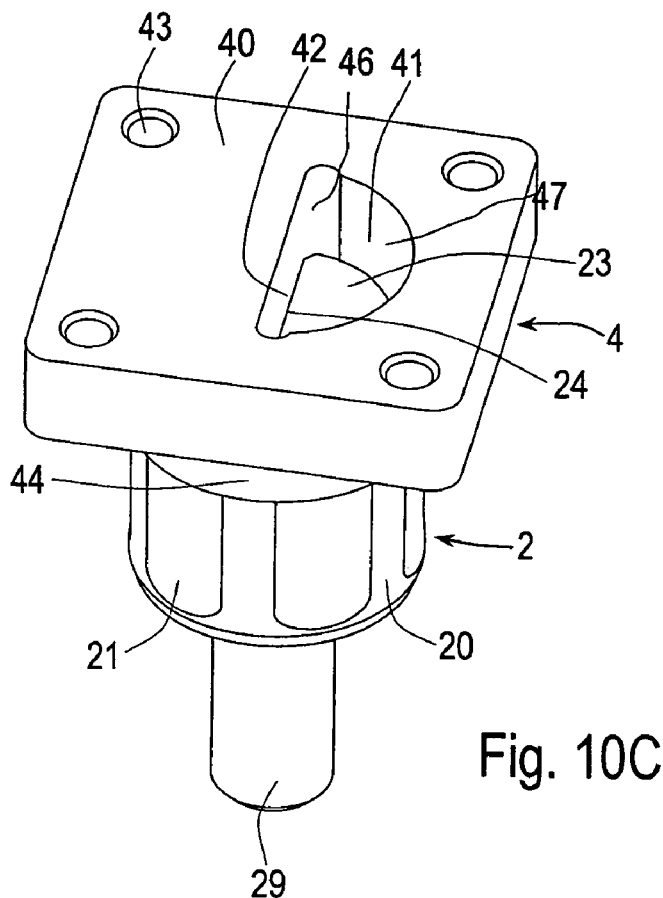
FIGS. 10c-e: show different perspective views of the connection between the transfer aid and the extension piece.
Figure 10D:
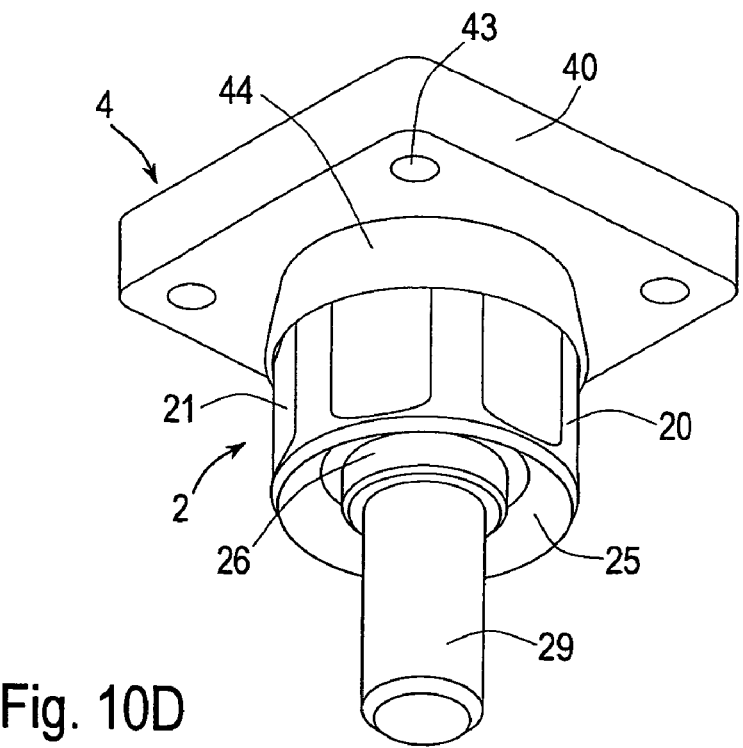

The transfer aid 4 snapped onto the extension piece 2 is shown in detail in FIGS. 10c and 10d. By engagement between the semicylinder section 23 and the opening 41, the position of the extension piece 2 relative to the circumferential direction is transferred to the transfer aid 4. The transfer aid can be fitted easily onto the extension piece by virtue of the bevel 27a on the extension piece and the recess 46 on the transfer aid. The circumferential position of the transfer aid relative to the extension piece is precisely defined by contact between the transfer surface 42 and the reference surface 24, on the one hand, and between the semicylindrical inner surface 47 of the transfer aid 4 and the semicylindrical outer surface 27b of the extension piece 2. The circular lip 44 of the transfer aid 4 essentially encloses the upper portion of the head part 20 of the extension piece 2.

Figure 10E:
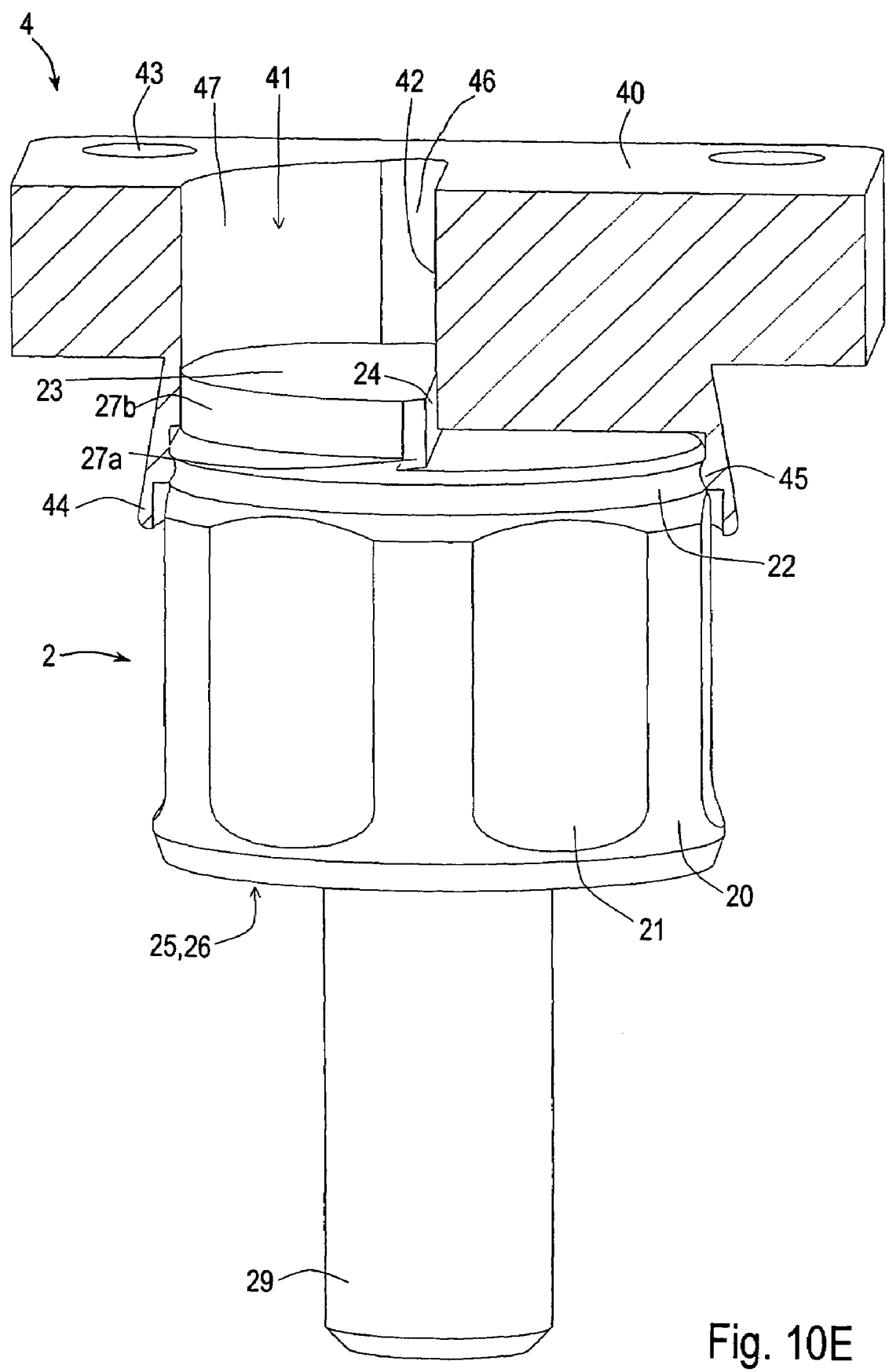

The engagement between the extension piece 2 and the transfer aid 4 is shown in detail and in cross section in FIG. 10e. The second contour 45 is formed by a radial bead. The bead snaps into the first contour 22, designed as a groove, of the extension piece 2. The semicircular cylinder section 23 lies in the opening 41, so that the reference surface 24 of the extension piece bears on the transfer surface 42 of the transfer aid 4.

Figure 11:
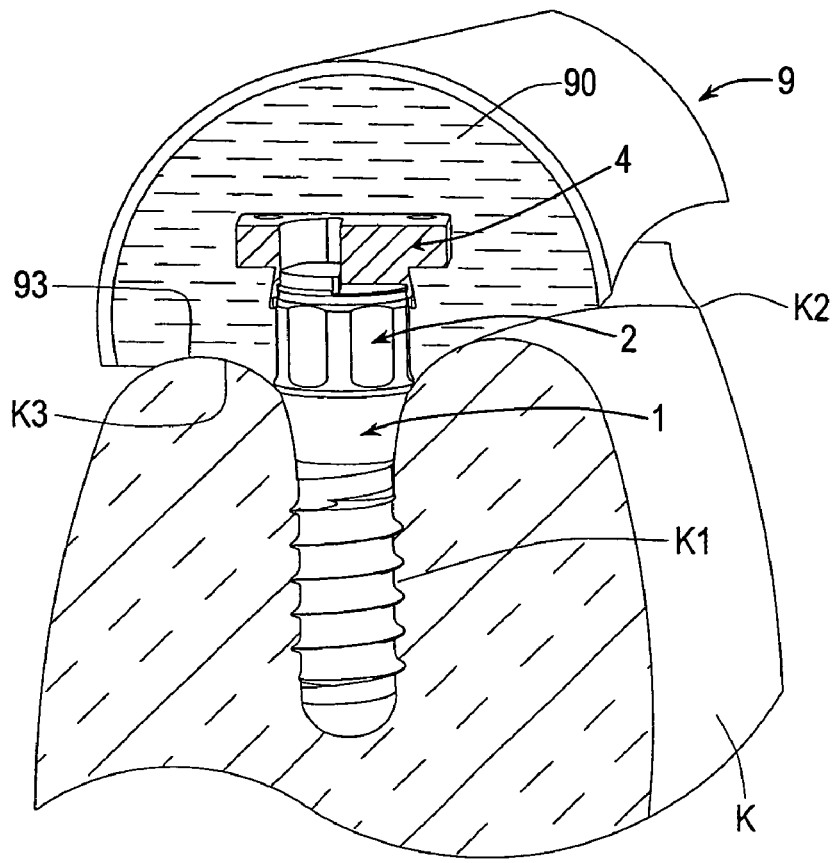

To take an impression, impression compound 90 in an impression tray 9 is pressed over the situation in the mouth with the implant 1 and, attached thereon, the extension piece 2 with transfer aid 4 (see FIG. 11). In this way, an impression 93 is formed. The elastomeric impression compound is typically vinyl polysiloxane/polyether rubber).

After the impression compound 90 has hardened, the impression 93 is removed from the extension piece 2. In this process, the transfer aid 4 remains in the impression compound 90, in particular because of the base plate 40, and, during removal of the impression 93, it separates from the extension piece 2 by virtue of the snap-fit connection.

Figure 12:
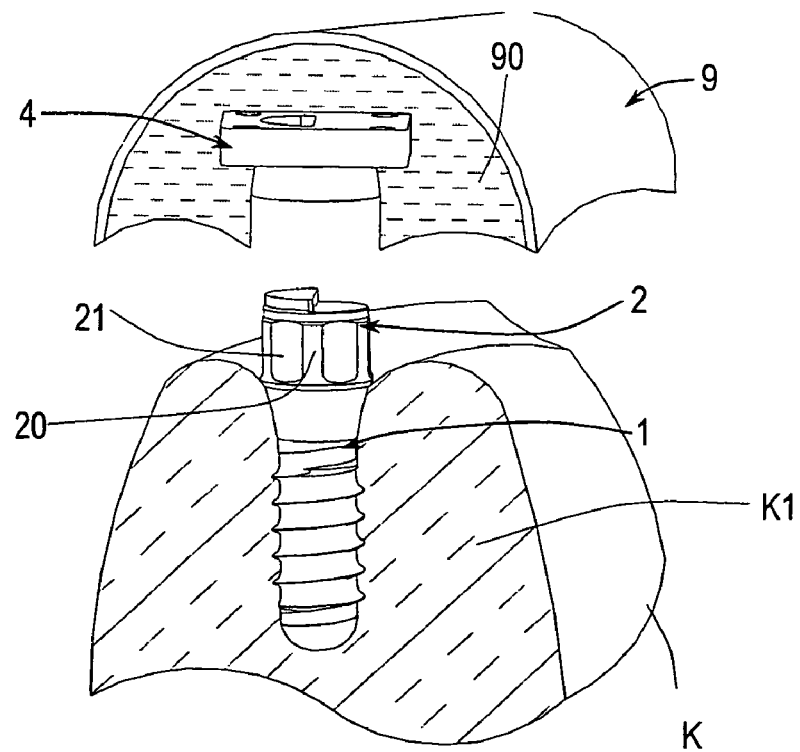

FIG. 12 shows the removal of the impression 9 from the implant 1 with the attached extension piece 2. The transfer aid 4 remains in the impression compound 90.

Figure 14A:
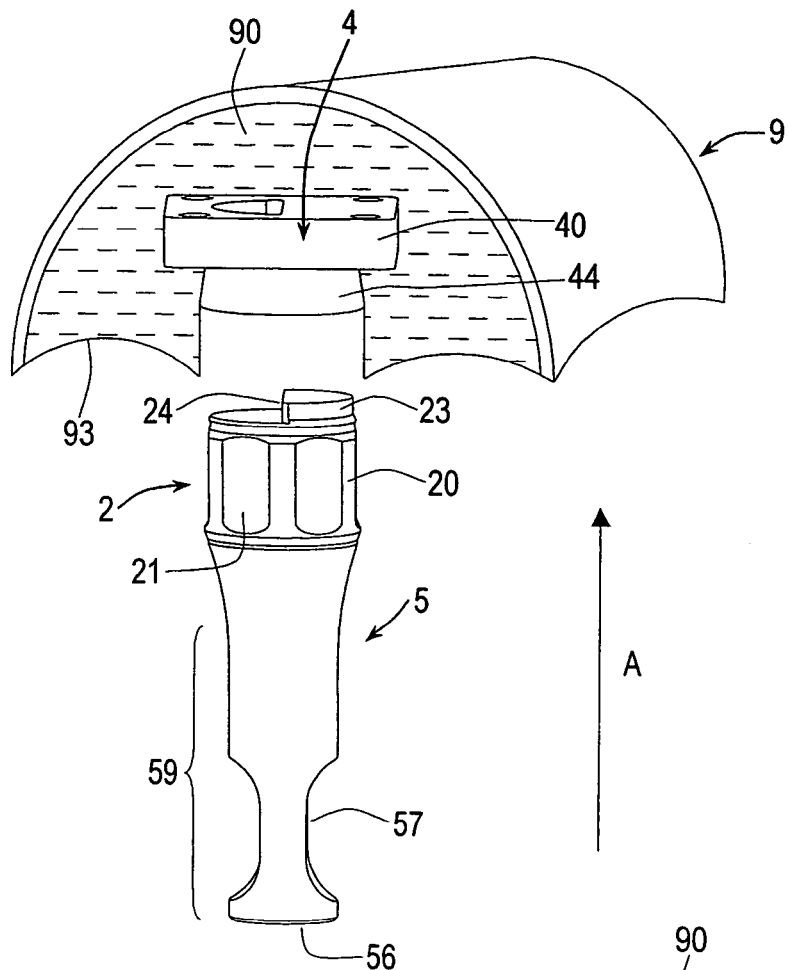
FIG. 14a: shows the repositioning of the extension piece with manipulation implant into the impression.
Figure 14B:
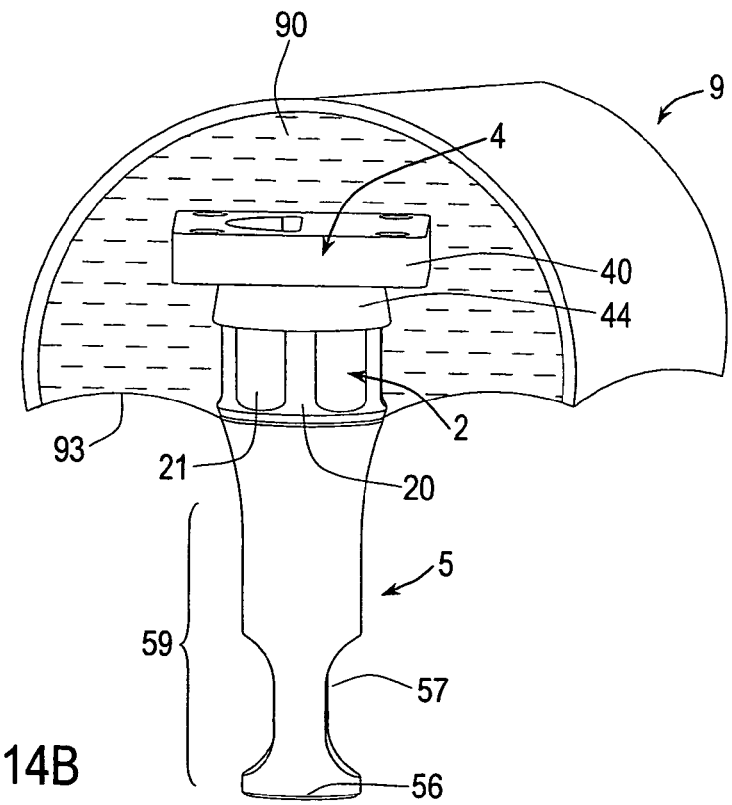
FIG. 14b: shows the extension piece with manipulation implant repositioned in the impression.

In a next step, the extension piece 2 is unscrewed from the implant with the screwing-in tool 3 (not shown). The screwing-in tool is then used to screw the extension piece 2 onto a manipulation implant (see FIG. 13a). FIG. 13b shows the extension piece 2 screwed onto the manipulation implant 5. In a next step (FIG. 14a), the manipulation implant 5, with the extension piece 2 screwed onto it, is repositioned in the impression 93. To do this, the semicircular cylinder section 23 has to be inserted into the opening 41 of the transfer aid 4 still held in the impression. To permit such repositioning, the manipulation implant 5 with extension piece 2 according to FIG. 14a has to be rotated 180° about the axis A of the extension piece 2, so that it can be inserted as shown in FIG. 14b. In an alternative embodiment, it is conceivable to firstly reposition the extension piece 2 and only then to screw in the manipulation implant 5.

The manipulation implant is screwed in with a relatively low torque without a torque tool. Typically, the manipulation implant is screwed in tight by hand without using a tool.

Figure 15A:
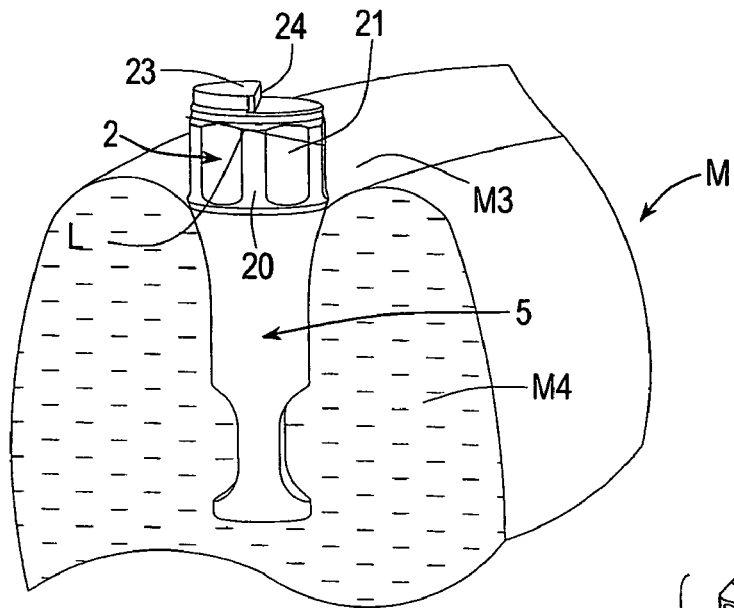
FIG. 15a: shows a perspective view of a working model with embedded manipulation implant and extension piece for application of a position marking.

FIG. 14b shows the impression of a single extension piece 2 with a manipulation implant 5. Of course, in one impression, impressions are taken of all the extension pieces 2 on all the implants 1 or abutments present. For simplification, only one implant/manipulation implant 5 with an extension piece 2 is shown. Starting from the impression 93 with the manipulation implants 5 secured therein (see FIG. 14b), a working model M is produced by casting the manipulation implants 5 into a modeling compound M4. In the working model M (see FIG. 15a), the heads 58 of the manipulation implants 5 are arranged in the same way as the heads 18 of the implants 1 in the patient's mouth. The working model M reproduces a positive contour M3 which corresponds to the peripheral contour K3 in the jaw area of the patient. Because of the transfer of the extension pieces 2 with the impression 93 and the transfer aid 4, the position of the extension pieces 2 in the working model M corresponds exactly to the position of the extension pieces 2 which have been screwed tightly onto the implant 1 with the predetermined first torque, typically 35 Ncm. To guarantee this, it is important to ensure that, in the repositioning step according to FIG. 14a, each individual extension piece 2 is repositioned at the correct location, i.e. that two extension pieces cannot be mixed up.

Figure 15B:
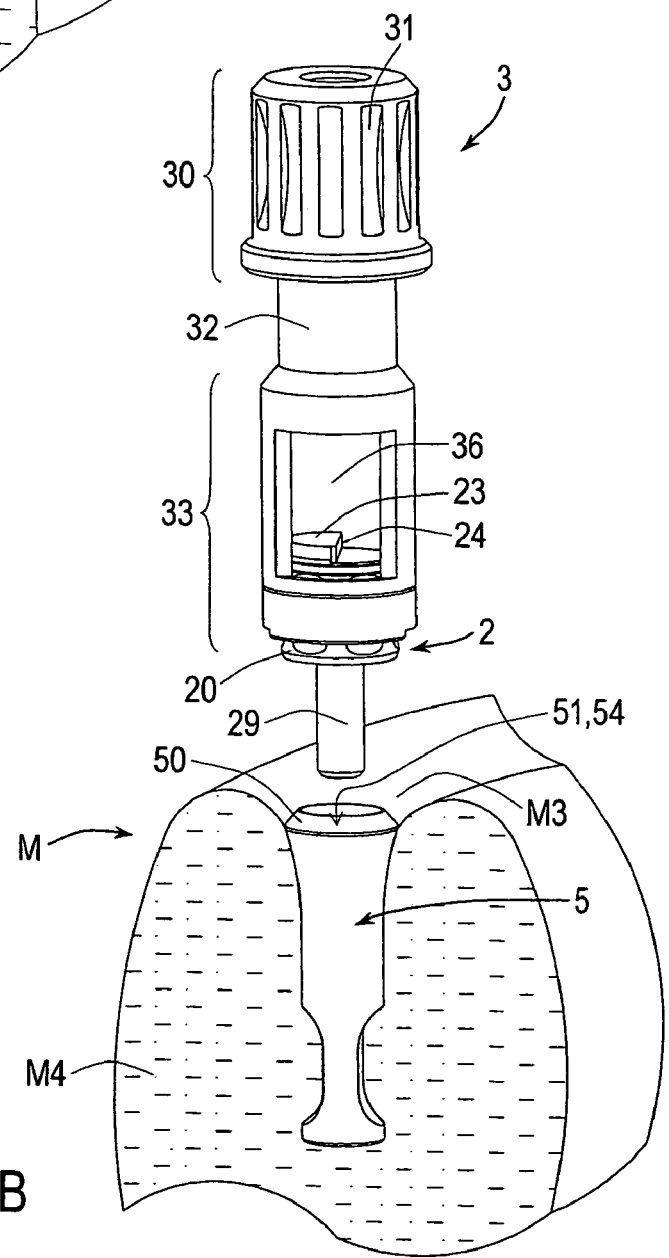
FIG. 15b: shows the removal of the extension piece from the manipulation implant.
Figure 16A:
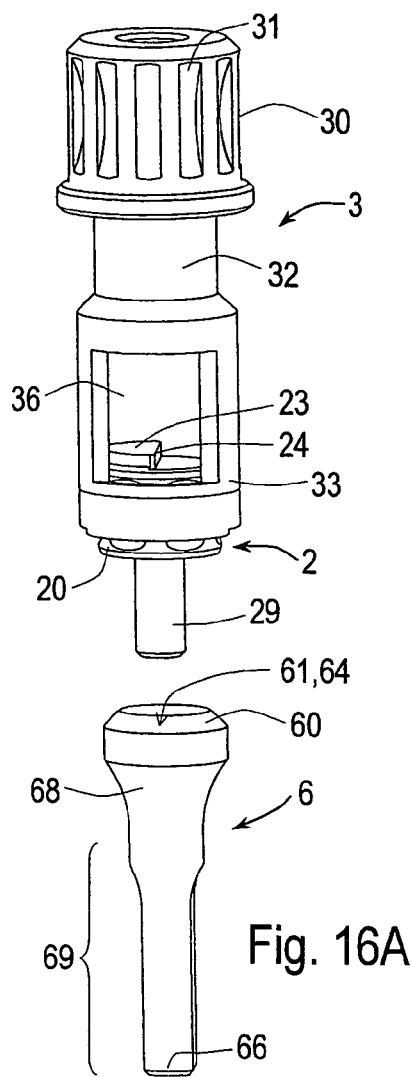
FIG. 16a: shows how the extension piece is screwed into a holder.
Figure 16B:
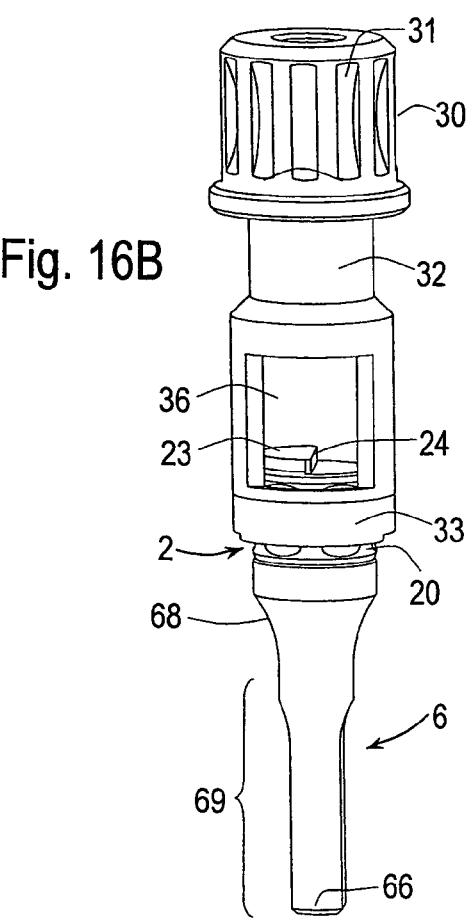
FIG. 16b: shows the extension piece screwed into the holder.

In a next step, a position marking L is arranged on the working model M. The position marking L defines the form to which the extension piece 2 is to be machined. The position marking L is chosen individually on each individual extension piece 2, so that the subsequent structure permits attachment of a tooth replacement in an exactly defined direction of application. After the position markings L have been arranged on all the extension pieces 2, the extension pieces, as shown in FIG. 15b, are removed from the working model M using the screwing-in tool 3. Then, as is shown in FIGS. 16a and 16b, the extension piece 2 is (or extension pieces 2 are) screwed onto holder(s) 6. The holder 6 serves to hold the extension pieces 2 precisely in a machining operation. The holder 6 protects the thread of the extension piece and also protects the fingers. It also affords better holding during machining of the extension piece.

Figure 17A:
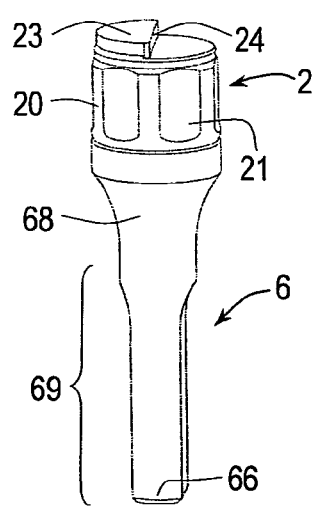
FIG. 17a: shows the extension piece with holder.
Figure 17B:
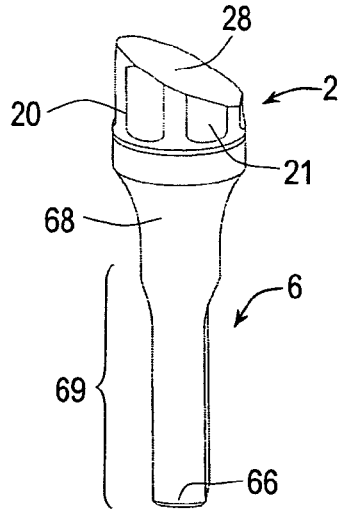
FIG. 17b: shows the machined extension piece with holder, FIGS. 18a+b: show the securing of a retention element.
Figure 18A:
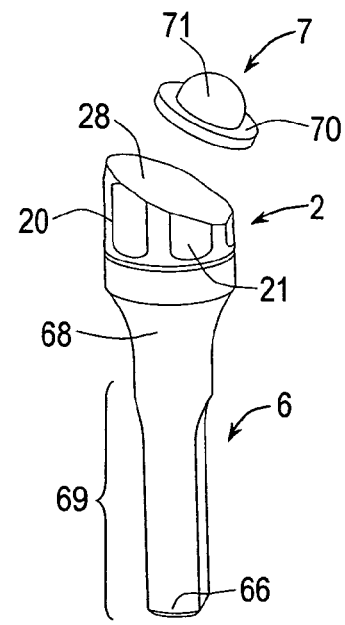

The extension piece 2 attached to the holder 6 (see FIG. 17a) is then ground along the position marking L so that a predefined, inclined plateau surface 28 is formed (see FIG. 17b). In a next step (see FIG. 18a), a retention element is secured on the inclined plateau surface 28, for example by soldering, lasering or casting.

Figure 18B:
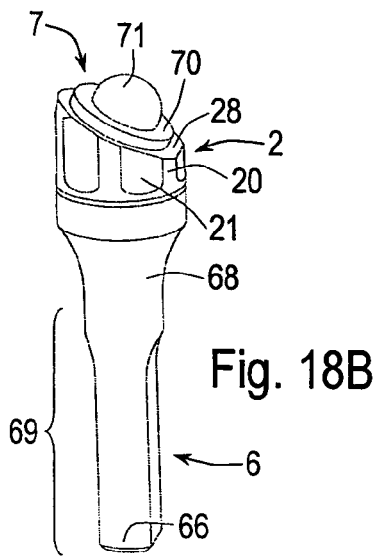
Figure 19B:
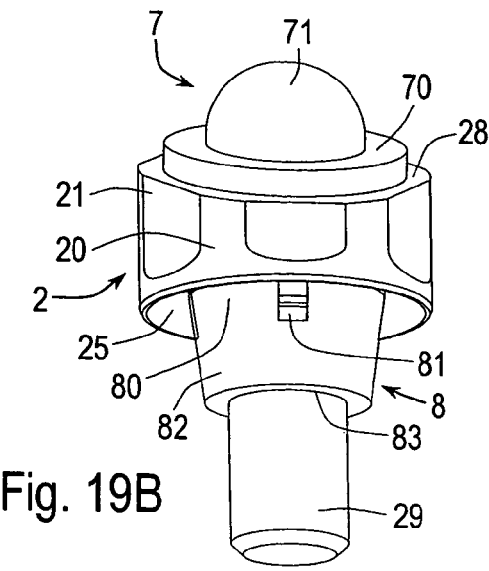
FIG. 19b: shows the extension piece with applied spreading cone and secured retention element.
Figure 19A:
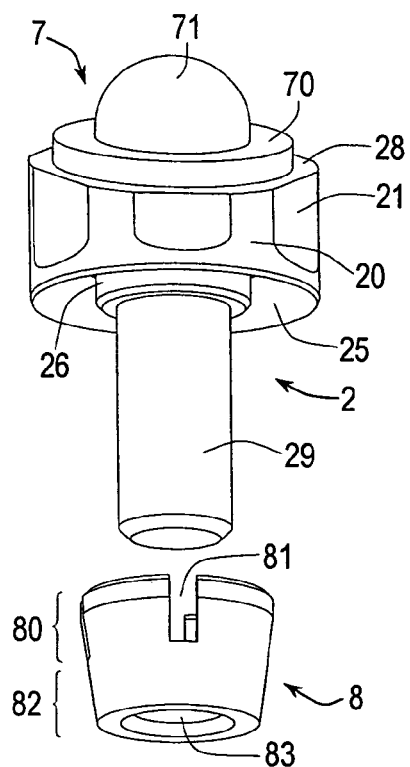
FIG. 19a: shows the application of a spreading cone onto the threaded stem of the extension piece.
Figure 20A:
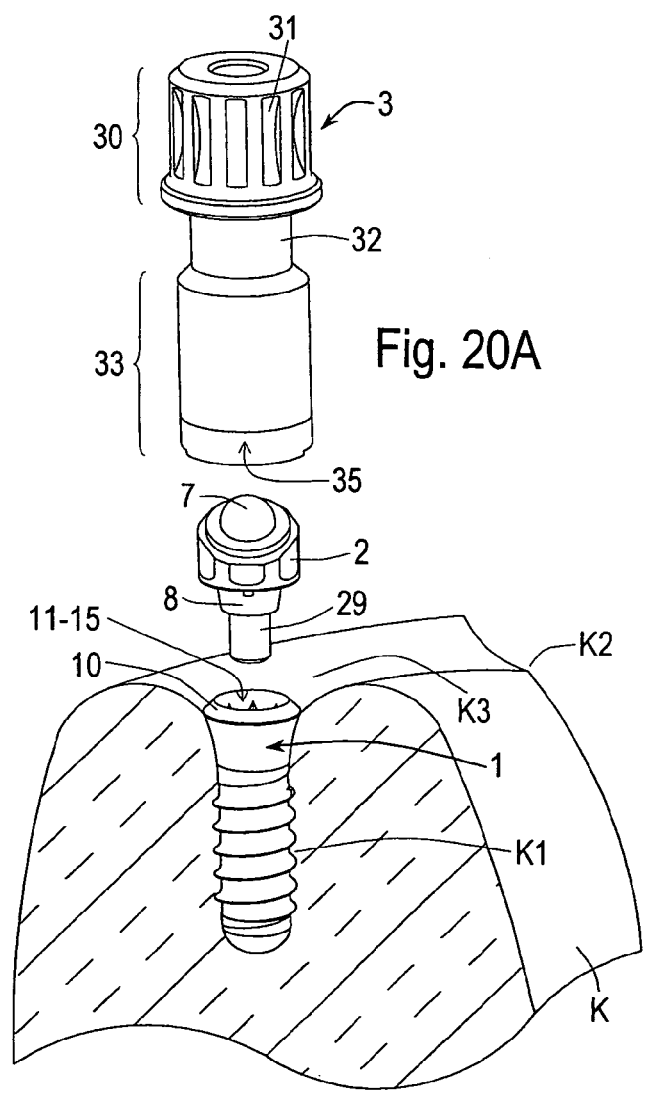
Figure 20B:
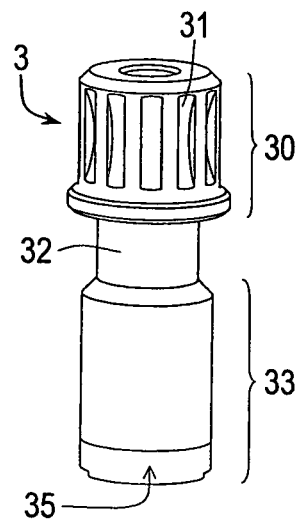
Figure 20C:
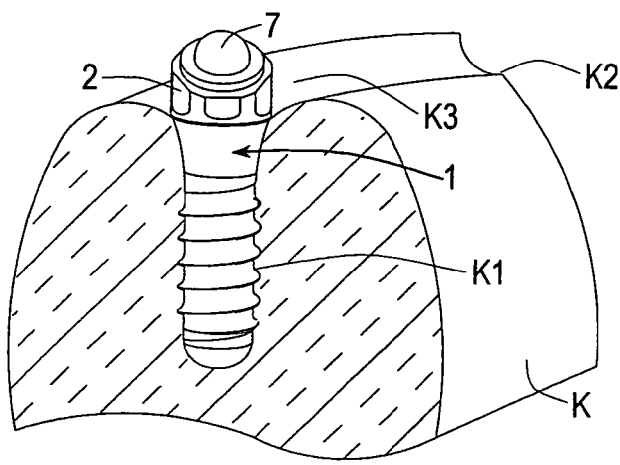
Figure 20C:
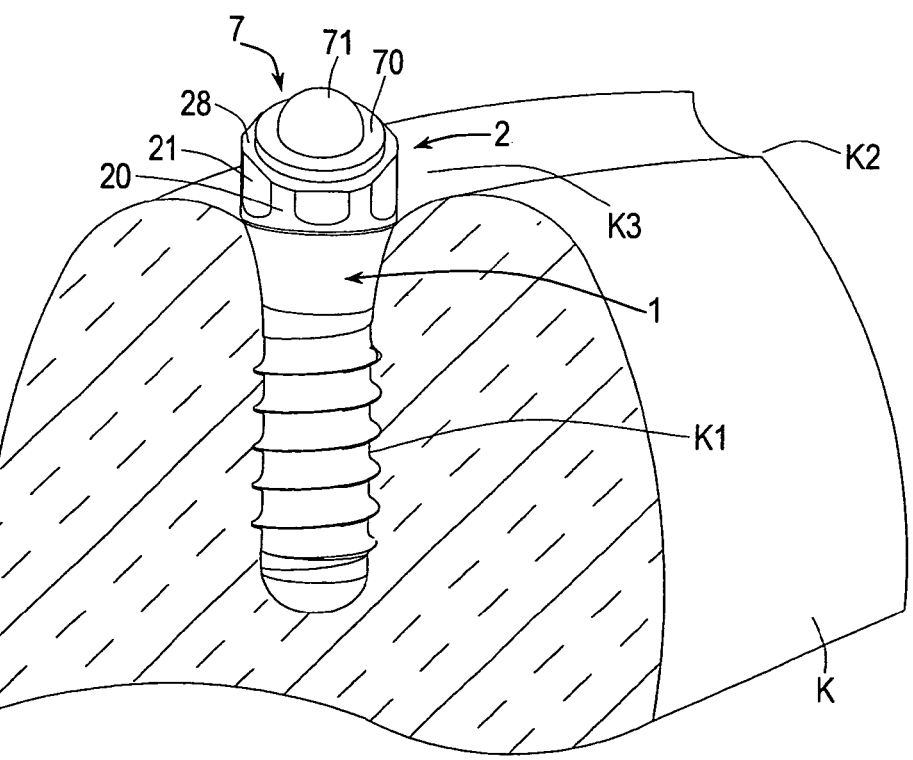

FIG. 18b shows the extension piece 2 with a retention element 70 secured on the plateau surface 28. The extension piece 2 is now removed from the holder 6 and is ready (see FIG. 19a) for definitive securing in the implant 1 in the patient's mouth. Before this securing, the spreading cone 8 is guided with the passage 83 over the threaded stem 29, so that it bears with the inner surface on the thickened portion 26 adjacent to the head part 20 of the machined extension piece 2 (see FIGS. 19a and 19b). The extension piece 2 provided in this way with the spreading cone 8 is screwed into the implant 1 in the patient's mouth, as shown in FIG. 20a. The screwing is once again effected using the screwing-in tool 3, which is provided with a suitable torque attachment. The extension piece 2 is screwed in with the first, predefined torque, typically 35 Ncm. This ensures that the position of the machined extension piece 2 in the implant 1 corresponds exactly to the position during impression-taking. FIG. 20c shows the situation in the mouth after attachment of the extension piece. By virtue of the individual machining of the inclined plateau surfaces 28 of each individual extension piece 2, it is possible to compensate for any lack of parallelism of the implants. The differently inclined plateau surfaces 28 of the different extension pieces 2 lie in parallel planes. In this way, a tooth replacement can be attached in a single direction of application.

Other embodiments of the invention will be apparent to those skilled in the art from consideration of the specification and practice of the invention disclosed herein. It is intended that the specification and examples be considered as exemplary only, with a true scope of the invention being indicated by the following claims.

The invention claimed is:

1. An extension piece for a dental implant comprising:
a head part which serves as a basis for a retention element, the head part having one end and a remote end,
a threaded stem arranged at said one end of the head part with which the extension piece can be screwed into the dental implant,
the head part being of substantially cylindrical design and having at said remote end at least one reference form, which defines the circumferential position of the extension piece and by which reference form the circumferential position of the extension piece can be transferred to a working model,
the head part having, between the reference form and the threaded stem, a plurality of non-cylindrical gripping surfaces by which the extension piece can be gripped and screwed into the dental implant with a tool engaging on the gripping surfaces,
the reference form comprising a semicyclindrical outer circumferential surface of a semicircular cylinder extending parallel to the screw axis of the extension piece and a substantially diagonally cut reference surface, and wherein a bevel is provided between the reference surface and the semicylindrical outer circumferential surface.

2. The extension piece as claimed in claim 1, wherein the extension piece has a mating shoulder via which the extension piece can be supported on an implant shoulder of the dental implant, such that the position of the extension piece in the axial direction can be transferred.

3. The extension piece as claimed in claim 1, wherein the extension piece has a first contour onto which a transfer aid with a complementarily shaped second contour can be clamped and/or snapped, and the first contour is arranged between the gripping surfaces and the reference form.

4. A transfer aid for transferring the position of dental implant and of the extension piece, as claimed in claim 3, to a working model, with the transfer aid comprising:
a transfer surface which defines the circumferential position of the transfer aid,
a base plate in which the transfer surface is arranged, the base plate having a non-cylindrical outer contour which can be anchored securely against rotation in an impression,
the transfer surface being shaped to complement the reference form of the extension piece and being part of a semicylindrical opening In the base plate,
a circular lip which is arranged on the base plate and which has a second contour by which the transfer aid can be snapped and/or clamped onto the first contour of the extension piece, and
wherein a recess is arranged in the transition area between the transfer surface and a semicylindrical inner surface of said semicylindrical opening in the base plate.

5. The transfer aid as claimed in claim 4, wherein the transfer aid is one piece.

6. The transfer aid as claimed in claim 5, made of a plastic material.

7. The transfer aid as claimed in claim 4, wherein the opening extends right through the base plate.

8. The transfer aid as claimed in claim 4, wherein the base plate is provided with holes which are arranged radially outside the circular lip.

9. The extension piece as claimed in claim 1, wherein the extension piece is made of a metallic, non-oxidizing, high-meting-point alloy.

10. The extension piece as claimed in claim 9, wherein the alloy is a composition of 60% Au, 19% Pt, 20% Pd, 1% Ir, the melting range being between 1400° and 1490° Celsius.

11. A method comprising:
providing an extension piece as claimed in claim 1, and which can be machined,
and using the extension piece as a transfer part for transferring its own axial and circumferential position to a working model and/or as a basis for a retention element.

12. A method for taking an impression of the radial and axial position of at least one dental implant implanted in a jaw bone with the extension piece as claimed in claim 1 fitted in it to a working model and/or for producing a basis for a retention element, said method comprising the following steps:
a) screwing the at least one extension piece with the reference form as a basis for a retention element into the at least one dental implant with a first torque,
b) producing an impression of the situation of the at least one dental implant and of the extension piece in the patient's mouth by applying an impression compound, the extension piece leaving an impression in the impression compound and remaining connected to the implant after removal of the impression compound from the mouth,
c) removing the extension piece from the implant after removal of the impression compound from the mouth,
d) repositioning the extension piece in the correct position in the impression,
e) before or after step d), screwing a manipulation implant with a second torque onto the at least one extension piece,
f) producing a working model by casting the manipulation implant or implants into a modeling compound, and wherein a position marking is arranged on the extension piece before machining, and wherein the extension piece, for machining, is removed from the working model and is fitted onto a holder and machined on the latter after the impression has been taken.

13. The method as claimed in claim 12, wherein a transfer aid is applied to the extension piece before the removal of the impression of the extension piece, and wherein the transfer aid remains in the impression compound when the impression is produced.

14. The method as claimed in claim 13, wherein the transfer aid is applied to the extension piece by clamping and/or screwing.

15. The method as claimed in claim 12, wherein the first torque is greater than the second torque, and wherein the second torque approximately corresponds to a manual screwing of the extension piece onto the manipulation implant.

16. The method as claimed in claim 12, wherein, in step a), the extension piece is turned twice in succession into the implant.

17. The method as claimed in claim 16, wherein the first torque is approximately 35 Ncm.

18. The method as claimed in claim 12, wherein during machining of the extension piece, a plateau surface is formed, to which a retention element for mounting a detachable tooth replacement is applied.

19. The method as claimed in claim 18, wherein the extension piece is screwed into the implant with the first torque.

20. The method as claimed in claim 18, wherein, upon definitive screwing of the machined extension piece into the implant, a spreading cone is inserted between an inner cone of the implant and the extension piece.

21. A method for taking an impression of the radial and axial position of at least one dental implant implanted in a jaw bone with the extension piece as claimed in claim 1 fitted in it to a working model and/or for producing a basis for a retention element, said method comprising the following steps:

a) screwing the at least one extension piece with a reference surface as a basis for a retention element into the at least one dental implant with a first torque, b) producing an impression of the situation of the at least one dental implant and of the extension piece in the patient's mouth by applying an impression compound, the extension piece leaving an impression in the impression compound and remaining connected to the implant after removal of the impression compound from the mouth, c) removing the extension piece from the implant after removal of the impression compound from the mouth, d) repositioning the extension piece in the correct position in the impression, e) before or after step d), screwing a manipulation implant with a second torque onto the at least one extension piece, wherein the first torque is greater than the second torque, and wherein the second torque approximately corresponds to a manual screwing of the extension piece onto the manipulation implant, and f) producing a working model by casting the manipulation implant or implants into a modeling compound, and wherein the extension piece is machined after the impression has been taken.

22. The method as claimed in claim 21, wherein, in step a), the extension piece is turned twice in succession into the implant.

23. The method as claimed in claim 21, wherein a position marking is arranged on the extension piece before the machining, and wherein the extension piece, for machining, is removed from the working model and in particular fitted onto a holder and machined on the latter.

24. The method as claimed in claim 23, wherein during machining of the extension piece, a plateau surface is formed, to which a retention element for mounting a detachable tooth replacement is applied.

25. The method as claimed in claim 23, wherein, upon definitive screwing of the machined extension piece into the implant, a spreading cone is inserted between an inner cone of the implant and the extension piece.

26. The method as claimed in claim 21, wherein the machined extension piece is screwed into the implant with the first torque.

* * * * *

UNITED STATES PATENT AND TRADEMARK OFFICE
CERTIFICATE OF CORRECTION

| | | |
|---|---|---|
| PATENT NO. | : 7,654,824 B2 | Page 1 of 1 |
| APPLICATION NO. | : 10/771572 | |
| DATED | : February 2, 2010 | |
| INVENTOR(S) | : Ebi et al. | |

It is certified that error appears in the above-identified patent and that said Letters Patent is hereby corrected as shown below:

Col. 13, Claim 3, line 4, "damped" should be -- clamped --.

Col. 13, Claim 9, line 3, "meting" should be -- melting --.

Col. 14, Claim 17, line 1, "16" should be -- 15 --.

Signed and Sealed this

Thirtieth Day of March, 2010

David J. Kappos
*Director of the United States Patent and Trademark Office*

UNITED STATES PATENT AND TRADEMARK OFFICE
CERTIFICATE OF CORRECTION

PATENT NO. : 7,654,824 B2  Page 1 of 1
APPLICATION NO. : 10/771572
DATED : February 2, 2010
INVENTOR(S) : Ebi et al.

It is certified that error appears in the above-identified patent and that said Letters Patent is hereby corrected as shown below:

Col. 13, Claim 3, line 34, "damped" should be -- clamped --.

Col. 13, Claim 9, line 67, "meting" should be -- melting --.

Col. 14, Claim 17, line 54, "16" should be -- 15 --.

This certificate supersedes the Certificate of Correction issued March 30, 2010.

Signed and Sealed this

Twenty-seventh Day of April, 2010

David J. Kappos
*Director of the United States Patent and Trademark Office*